United States Patent [19]

Boedecker

[11] 3,965,900

[45] June 29, 1976

[54] ANTI-REFLUX DEVICE

[75] Inventor: Steven M. Boedecker, McHenry, Ill.

[73] Assignee: The Kendall Company, Boston, Mass.

[22] Filed: Oct. 2, 1974

[21] Appl. No.: 511,569

[52] U.S. Cl. .............................. 128/275; 128/294; 137/525.1
[51] Int. Cl.[2] ............................................ A61F 5/44
[58] Field of Search .... 128/275, 294, 295, DIG. 24, 128/274; 137/525, 525.1

[56] References Cited
UNITED STATES PATENTS

| | | | |
|---|---|---|---|
| 2,755,060 | 7/1956 | Twyman........................ | 128/274 UX |
| 3,477,438 | 11/1969 | Allen et al..................... | 128/349 BU |
| 3,525,357 | 8/1970 | Koreski......................... | 128/274 UX |
| 3,529,599 | 9/1970 | Folkman et al................ | 128/275 |
| 3,564,620 | 2/1971 | Clark............................. | 128/295 |
| 3,586,041 | 6/1971 | Monestere..................... | 128/295 |
| 3,716,055 | 2/1973 | Schultze........................ | 128/275 |
| 3,734,080 | 5/1973 | Petterson et al. ............. | 128/2 F |
| 3,901,235 | 8/1975 | Patel et al..................... | 128/275 |

Primary Examiner—John D. Yasko
Attorney, Agent, or Firm—Powell L. Sprunger

[57] ABSTRACT

An anti-reflux device for a collection bag having an inlet port communicating with the inside of the bag and a generally planar surface surrounding the port on the inside of the bag. The device has a thin flexible valve element having sufficiently large dimensions to cover the inlet port, and means for retaining the valve element adjacent the surface on the inside of the bag in a sliding relationship with the inlet port and with the valve element covering the port.

17 Claims, 9 Drawing Figures

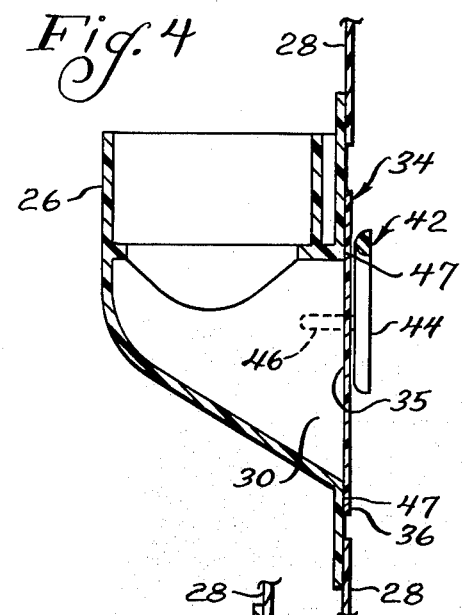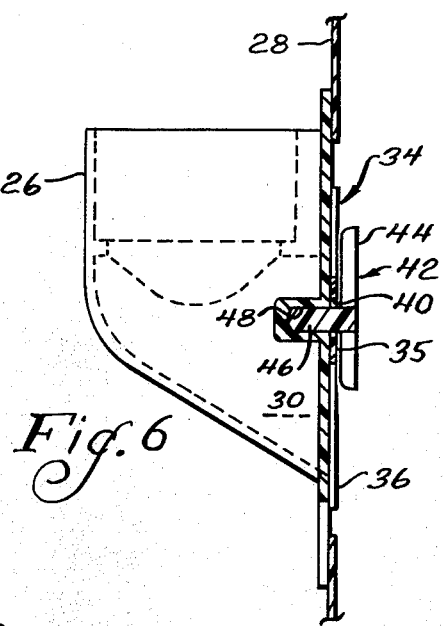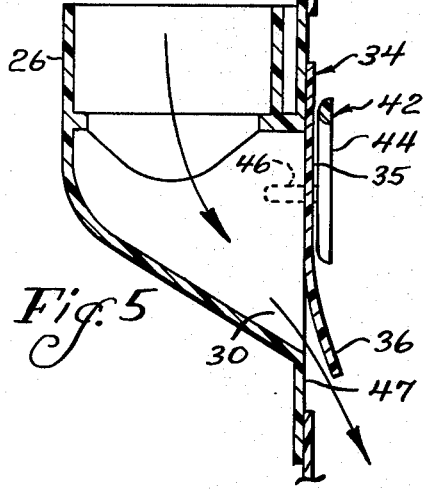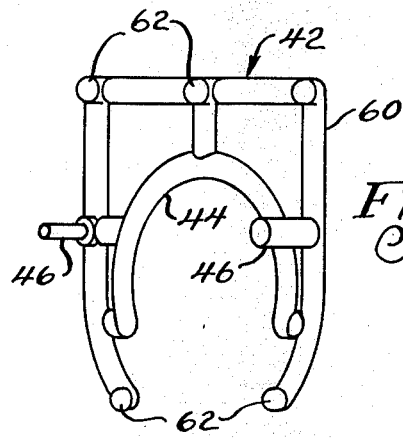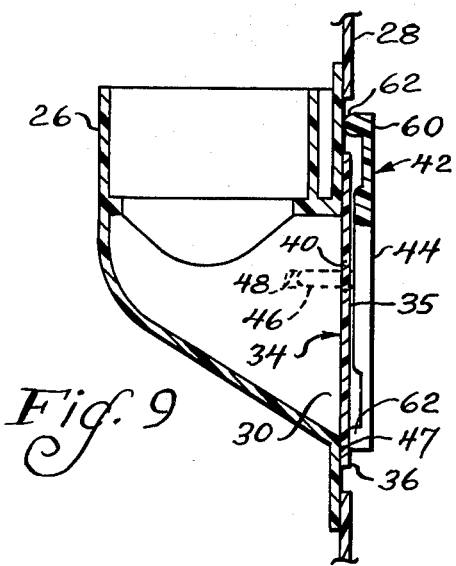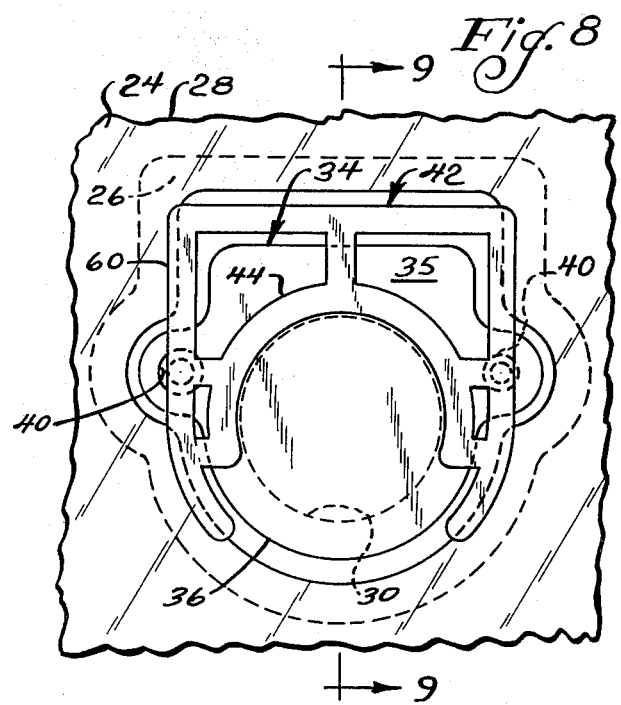

ANTI-REFLUX DEVICE

BACKGROUND OF THE INVENTION

The present invention relates to collection bags, and more particularly to anti-reflux devices for such bags.

The systems in common use for urinary catheterization of a patient usually are provided with a catheter, a drainage tube, and a collection receptacle. The catheter is positioned in the patient with its distal end received in the patient's bladder and its proximal end extending outside the patient's body. The drainage tube is connected between the proximal end of the catheter and the collection receptacle. During catherization, urine drains through the catheter and drainage tube to the receptacle for collection. During recent years collection receptacles having flexible side walls have come into widespread use. Although such flexible receptacles or bags may have many advantages over the previously used rigid containers, a danger which has been attendant with the use of such bags is that pressure exerted against the side walls of the flexible bag may cause a reflux of urine from the bag into the drainage tube, and possibly the catheter and patient's bladder. The reflux of urine may be caused by the inadvertent bumping, squeezing, or tipping of the bag by a nurse, a physician, a visitor of the patient, or the patient himself. The urine which refluxes from the bag into the drainage tube causes an increase of pressure in the patient's bladder, and may result in trauma to the bladder. Additionally, the refluxing urine dramatically increases the possibility of retrograde bacterial movement from the bag to the patient's bladder, with possible deleterious results to the patient.

It has been proposed that a flexible valve be sealed around an inlet port communication between the tube and the bag to solve the reflux problem. However, it has been discovered that during sealing of the valve and subsequent sterilization of the bag the valve may become distorted, and, accordingly, may malfunction during later use.

SUMMARY OF THE INVENTION

A principal feature of the present invention is the provision of an anti-reflux device for a collection bag of simplified and improved reliability.

The collection bag has a connector secured to a wall of the bag, with the connector having an inlet port communicating with the inside of the bag. The anti-reflux device of the present invention includes a thin flexible valve element having sufficiently large dimensions to cover the inlet port. The device also has a retaining member for retaining the valve element over the port in a floating relationship with the connector and port.

Thus, a feature of the invention is that the valve element flexes to permit passage of fluid from the connector through the port to the inside of the bag.

Another feature of the invention is that the valve element closes the port responsive to pressure inside the bag to prevent passage of fluid from the inside of the bag to the connector.

A further feature of the invention is that the valve element is permitted to float relative the connector and port without affecting its sealing characteristics to prevent reflux of urine from the bag.

Yet another feature of the invention is that the sealing characteristics of the floating valve element are unaffected by sterilization of the collection bag.

Another feature of the invention is that in one embodiment the retaining member covers a sufficient portion of the valve element to prevent contact of the valve element with the opposite wall of the bag relative the connector.

Further features of the invention will become more fully apparent in the following description of the embodiments of this invention and from the appended claims.

DESCRIPTION OF THE DRAWINGS

In the drawings:

FIG. 4 is a fragmentary sectional view taken substantially as indicated along the line 4—4 of FIG. 3, showing a valve element in the anti-reflux device in a closed position to prevent reflux of liquid from the bag into a connector of the device;

FIG. 5 is a sectional view of the anti-reflux device of FIG. 4, showing the valve in an open position to permit passage of liquid from the connector to the inside of the bag;

FIG. 6 is a fragmentary sectional view taken substantially as indicated along the line 6—6 of FIG. 3;

FIG. 7 is a perspective view of a retaining element in another embodiment of the anti-reflux device of the present invention;

FIG. 8 is a fragmentary plan view, taken from the inside of the bag, of an embodiment of the anti-reflux of the present invention incorporating the retaining member of FIG. 7; and FIG. 9 is a fragmentary sectional view taken substantially as indicated along the line 9—9 of FIG. 8.

DESCRIPTION OF THE PREFERRED EMBODIMENTS

Figure 1:
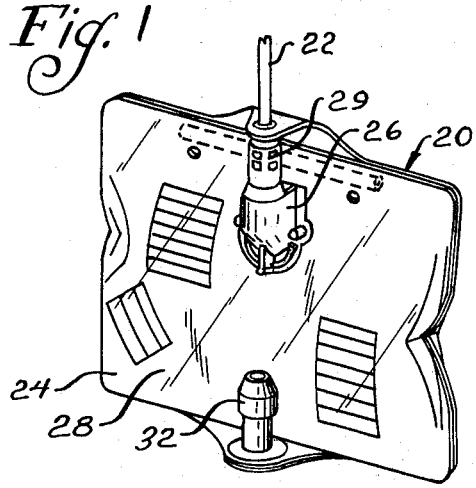
FIG. 1 is a fragmentary propsective view of a drainage tube and collection bag in a liquid drainage system.
Figure 2:
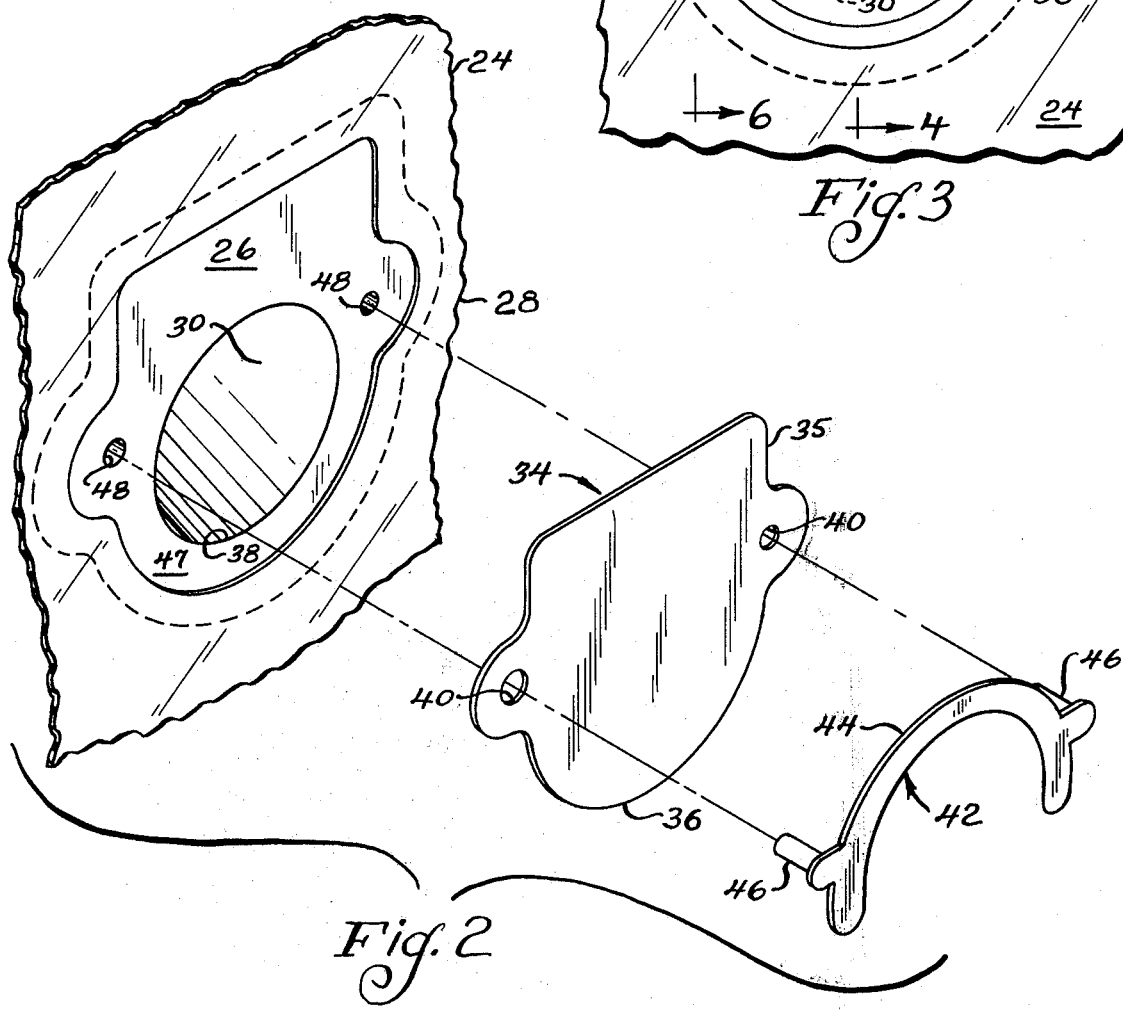
FIG. 2 is an exploded view of one embodiment of an anti-reflux device of the present invention for use in the drainage bag of FIG. 1.

Referring now to FIG. 1, there is shown a liquid drainage system designated generally 20, having a drainage tube 22 and a liquid collection bag 24. The drainage tube 22 is connected to and communicates with a connector or a drip chamber 26 which is secured to a wall 28 of the bag 24, and which preferably has a filtered vent 29. The connector 26 communicates with the inside of the bag through an inlet port 30, as shown in FIG. 2. During catheterization the drainage tube 22 is connected to the proximal end of a catheter (not shown) which has its distal end positioned in the bladder of a patient, such that urine drains from the patient's bladder through the drainage tube 22 and the connector 26 into the bag 24 for collection. The bag 24 may have valve means 32 adjacent its lower end for drainage of the bag.

One embodiment of an anti-reflux device of the present invention is illustrated in FIG. 2–6. The anti-reflux device includes a thin flexible valve element 34 which may be made of a plastic material or an elastomer, e.g., rubber. The valve element 34 has sufficiently large dimensions to cover the inlet port 30, and preferably has a generally rectangular portion 35 and a depending lip 36 of generally semi-circular shape to cover the lower portion 38 of the port 30 relative the top of the bag. The valve element also has a pair of spaced apertures 40 which are located on opposite sides of the inlet port 30 and adjacent the upper end of the port when the valve element 34 is in place over the port.

Figure 3:
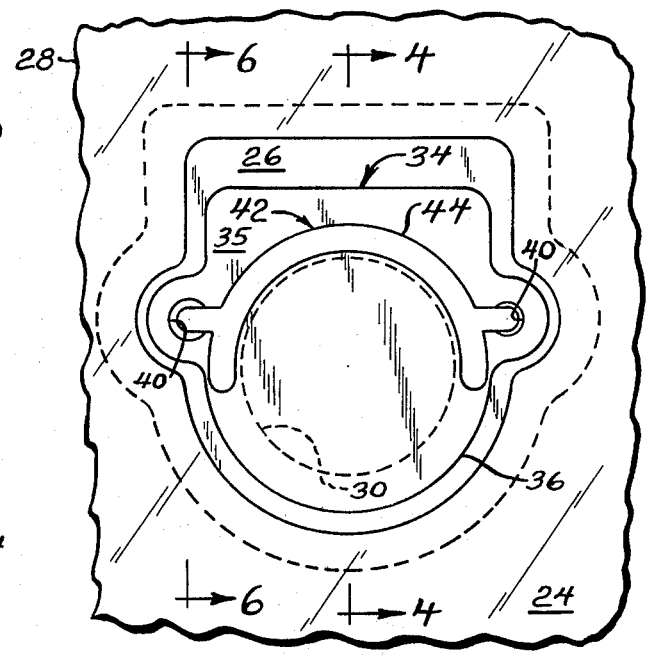
FIG. 3 is a fragmentary plan view of the anti-reflux device of FIG. 2 taken from the inside of the bag.

The anti-reflux device also has a retaining member 42 having a semi-annular rim 44 and a pair of spaced pins 46 corresponding to the apertures 40 of the valve element 34. The pins 46 of the retaining member 42 are received through the apertures 40 of the valve element 34 into a pair of spaced bores 48 in the connector 26 which extend from the inside of the bag, in order to capture and retain the valve element 34 in place over a planar surface 47 surrounding the inlet port 30. With the valve element 34 retained in place by the retaining member 42, the rim 44 of the retaining member 42 extends around the upper edge of the port 30, as best shown in FIG. 3. As illustrated in FIG. 5, the lip 36 of the valve element 34 flexes away from the connector 26 to permit passage of liquid from the connector 26 through the inlet port 30 to the inside of the bag. However, if a force is exerted against the valve element 34 from the inside of the bag, the valve element sealingly engages against the surface 47 of the connector 26 and closes the inlet port 30, as shown in FIG. 4. Such force may be caused by an increase of pressure in the bag due to squeezing of the bag, or by tilting of the bag causing the collected urine to contact the valve element 34. Thus, the valve element 34 prevents the reflux of urine from the bag into the connector 26 and drainage tube 22.

As best shown in FIG. 6, the size of the apertures 40 in the valve element 34 are larger than the cross-sectional size of the pins 46 of the retaining member 42 and the rim 44 is spaced slightly from the valve element 34, such that the valve element 34 is permitted to move laterally relative the connector 26 and inlet port 30. Thus, the valve element 34 is permitted to float or slide slightly over the connector and port without affecting the capability of the valve element 34 to open and close the port 30. It has been found that sterilization of the bag may cause a slight change in shape of the various components of the bag, which may be made of different materials, relative the shape of the components prior to sterilization. If the valve element is sealed to the connector, such sterilization may cause a distortion of the valve element and a malfunction of the anti-reflux mechanism during use. In contrast, according to the present invention, the valve element 34 of the anti-reflux device is permitted to float relative the port 30 and the connector 26, in order that the valve element and connector may independently assume a different shape during sterilization without degrading the operation of the valve element in opening and closing the port. Moreover, if the valve element is sealed to the connector, the valve element may become distorted during the sealing operation, such that the valve element may fail to function properly during use. Since the valve element 34 in the anti-reflux device of the present invention is not sealed to the connector, such distortion of the valve element does not take place. Thus, there has been described a new and improved anti-reflux device for a collection bag which retains excellent sealing characteristics irrespective of sterilization or other treatment to the bag. In addition, the retaining member 42 serves to protect the valve element 34 from damage during packaging, transportation, storage, and use.

Referring now to FIGS. 7–9, there is shown another embodiment of the anti-reflux device of the present invention which is similar in most respects to the device described in connection with FIGS. 1–6, and in which like reference numerals designate like parts. The retaining member 42 in this embodiment also has a semi-annular rim 44 and a pair of spaced pins 46 which are received through apertures 40 in the valve element 34 and into bores 48 in the connector 26 to retain the valve element 34 in place over the port 30, as previously described in connection with FIGS. 1–6, and the size of the apertures 40 is greater than the cross-sectional size of the pins 46 of the retaining member 42 to permit flotation of the valve element 34 relative the port 30 and the connector 26.

However, the retaining member 42 differs in that it includes an outer frame portion 60 connected to and extending around the inner rim 44, as best shown in FIG. 7. As illustrated in FIGS. 7 and 9, the frame portion 60 has a plurality of protuberances 62 disposed around the frame portion 60 and facing toward the valve element 34 and connector 26. The protuberances 62 provide stability to the retaining member 42 and maintain the retaining member in a spaced relationship with the valve element 34. As shown in FIGS. 8 and 9, the retaining member 42 covers a sufficient portion of the valve element 34 to prevent contact of the valve element with the opposite wall of the bag 24 relative the wall 28 and connector 26. Certain of the valve elements, such as a valve element made of rubber, may have a deleterious effect upon the opposite wall of the bag if contact between the valve element and the wall is permitted, due to migration of plasticizers from the wall to the rubber valve. Thus, the retaining member 42 of the anti-reflux device of FIGS. 7–9 prevents contact between the valve element 34 and the opposite wall of the bag to prevent damage to the opposite wall. In other respects, the anti-reflux device of FIGS. 7–9 operates very similar to the device described in connection with FIGS. 1–6.

It will be understood that other embodiments of the anti-reflux device are contemplated to be within the scope of the invention. For example, the retaining member or retaining means 42 may comprise a pair of spaced posts or pins extending from the connector 26 towards the inside of the bag, with the posts being received in the apertures 40 of the valve element 34. Such posts may have enlarged ends to retain the valve element 34 in place over the inlet port 30. in another embodiment, the retaining member 42 may have an annular rim which extends completely around the inlet port 30.

The foregoing detailed description is given for clearness of understanding only, and no unnecessary limitations should be understood therefrom, as modifications will be obvious to those skilled in the art.

I claim:

1. An anti-reflux device for a collection bag having an inlet port communicating with the inside of the bag and a generally planar surface surrounding the port on the inside of the bag, comprising:

a thin flexible valve element having sufficiently large dimensions to cover the inlet port; and
means for retaining said valve element adjacent said surface on the inside of the bag in a slidable relationship with the inlet port and with the valve element covering the port, with said valve element flexing away from the surface to permit passage of fluid through the inlet port into the inside of the bag, and with said valve element sealingly engaging against said surface responsive to pressure in the bag to prevent reflux of fluid from the bag to the inlet port.

2. The anti-reflux device of claim 1 wherein said valve element includes a pair of spaced apertures, and in which the retaining means includes a pair of spaced pins received through said apertures, with the size of said apertures being greater than the cross-sectional size of the pins, whereby the valve element is permitted to move laterally relative the port.

3. An anti-reflux device for a collection bag, comprising:
   a connector secured to a wall of said bag and having an inlet port communicating with the inside of the bag;
   a thin flexible valve element having sufficiently large dimensions to cover said inlet port; and
   means for retaining said valve element over the port in a floating relationship with the connector and port, with said valve element flexing to permit passage of fluid from the connector through the port to the inside of the bag, and with said valve element closing the port responsive to pressure inside the bag to prevent passage of fluid from the inside of the bag to the connector.

4. The anti-reflux device of claim 3 wherein said valve element is made from a plastic material.

5. The anti-reflux device of claim 3 wherein said valve element is made from rubber.

6. The anti-reflux device of claim 3 wherein said connector comprises a drip chamber.

7. The anti-reflux device of claim 3 wherein the retaining means comprises a retaining member being positioned with the valve element located intermediate the retaining member and said connector.

8. The anti-reflux device of claim 7 wherein said valve element includes a pair of spaced apertures, and said retaining member includes a pair of spaced pins received through said apertures, with the size of said apertures being greater than the cross-sectional size of the pins, whereby the valve element is permitted to move laterally relative the port.

9. The anti-reflux device of claim 8 wherein the connector includes a pair of spaced bores to receive the pins of the retaining member.

10. The anti-reflux device of claim 8 wherein the apertures and pins are located on opposite sides of the port and adjacent the upper end of the port relative the top of the bag.

11. The anti-reflux device of claim 7 wherein the inlet port has a generally circular shape, and said retaining member includes a generally semi-annular rim disposed around the upper edge of the port relative the top of the bag.

12. The anti-reflux device of claim 7 wherein the retaining member covers a sufficient portion of the valve element to prevent contact of the valve element with the opposite wall of the bag relative the connector.

13. The anti-reflux device of claim 7 wherein the retaining member includes a plurality of protuberances facing toward the valve element.

14. The anti-reflux device of claim 3 wherein the valve element has a generally rectangular portion and a depending lip having a generally semi-circular shape to cover the lower portion of the port relative the top of the bag.

15. The anti-reflux device of claim 3 wherein said connector includes a filtered vent.

16. An anti-reflux device for a collection bag, comprising:
   a connector secured to a wall of the bag, said connector having an inlet port communicating with the inside of the bag and a pair of spaced bores extending from the inside of the bag, said bores being located on opposite sides of the port and adjacent the upper end of the port relative to the top of the bag;
   a thin flexible valve element having a pair of spaced apertures corresponding to the connector bores and having sufficiently large dimensions to cover the port when the apertures are located over the bores; and
   a retaining member having a pair of spaced pins received through the apertures of the valve element into the bores of the connector to retain the valve element in place over said port, with the size of the apertures being greater than the cross-sectional size of the pins to permit flotation of the valve element relative the connector and port, said retaining member having a rim disposed around the upper edge of the port relative the top of the bag, whereby the valve element flexes to permit passage of fluid from the connector to the inside of the bag, and the valve element closes the port responsive to pressure inside the bag to prevent passage of fluid from the inside of the bag to the connector.

17. The anti-reflux device of claim 16 wherein the valve element has a generally rectangular portion and a depending lip of generally semi-circular shape to cover the lower portion of the port relative the top of the bag.

* * * * *